United States Patent [19]

Wei et al.

[11] 3,947,439
[45]*Mar. 30, 1976

[54] 4-HYDROXY-4-PHENYL-2,3-CYCLOALKYLIMINO-2-THIAZOLIDINEALKYLCARBOXYLIC ACID LACTONES

[75] Inventors: Peter H. L. Wei, Springfield; Stanley C. Bell, Penn Valley, both of Pa.

[73] Assignee: American Home Products Corporation, New York, N.Y.

[ * ] Notice: The portion of the term of this patent subsequent to Dec. 10, 1991, has been disclaimed.

[22] Filed: Nov. 14, 1974

[21] Appl. No.: 523,762

Related U.S. Application Data

[63] Continuation-in-part of Ser. No. 346,495, March 30, 1973, abandoned.

[52] U.S. Cl....... 260/251 A; 260/306.7 R; 424/251; 424/270
[51] Int. Cl.$^2$........................................ C07D 513/14
[58] Field of Search ................. 260/251 A, 306.7 T

[56] References Cited
UNITED STATES PATENTS
| | | | |
|---|---|---|---|
| 3,704,304 | 11/1972 | Wei et al. | 260/256.5 R |
| 3,853,872 | 12/1974 | Wei et al. | 260/251 A |

OTHER PUBLICATIONS

Fieser et al., Advanced Organic Chemistry, Reinhold Publishing Co., N.Y., 1961, p. 574.

Noller, Chemistry of Organic Compounds, W. B. Saunders Co., Philadelphia (1965), p. 858.

*Primary Examiner*—R. Gallagher
*Assistant Examiner*—Diana G. Rivers
*Attorney, Agent, or Firm*—David E. Frankhouser

[57] ABSTRACT

Compounds of the formula:

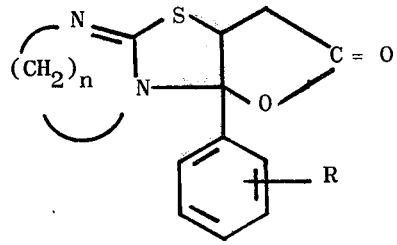

wherein R is hydrogen, lower alkyl, halogen, nitro, trifluoromethyl, or lower alkoxy; and $n$ is 2, 3, or 4; and the non-toxic pharmaceutically acceptable acid addition salts thereof; have CNS-depressant activity.

3 Claims, No Drawings

4-HYDROXY-4-PHENYL-2,3-CYCLOALK-YLIMINO-2-THIAZOLIDINEALKYLCARBOXYLIC ACID LACTONES

This is a continuation-in-part of application Ser. No. 346,495, filed Mar. 30, 1973, and now abandoned.

The invention sought to be patented comprises chemical compounds having the structural formula:

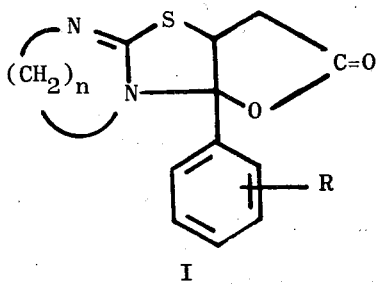

I wherein R is hydrogen, lower alkyl, halogen, nitro, trifluoromethyl, or lower alkoxy; and n is 2, 3, or 4; and the non-toxic pharmaceutically acceptable acid addition salts thereof.

As used herein the term "lower alkyl" or "lower alkoxy" means a substituent having an alkyl moiety of from one to four carbons. The term "halogen" means a chloro, bromo, or iodo substituent.

The compounds of Formula I, where R and n are hereinbefore defined, exert a depressant action on the central nervous system as demonstrated by evaluation in standard pharmacological test procedures. In addition to their CNS-depressant effects, the compounds of Formula I, wherein R is chloro, n is 3 or 4, antagonize reserpine-induced ptosis in mice, evidencing moodelevating activity.

The compounds of Formula I are prepared by the reaction of a compound of Formula II:

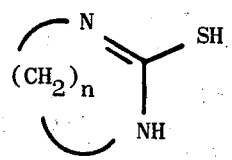

II where n is 2, 3, or 4; with a compound of Formula III:

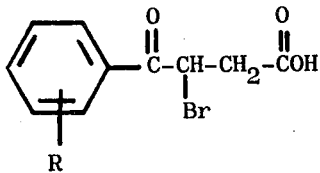

III where R has the meaning as defined in Formula I.

The reaction is carried out in acetic anhydride or in glacial acetic acid in the presence of acetic anhydride. The reaction is performed at an elevated temperature, such as at steam bath temperatures. The reaction product is isolated as the hydrobromide salt. If desired, the salt can be neutralized with a suitable base to give the free base, or it can be converted to other non-toxic, pharmaceutically acceptable salts by conventional procedures, such as by treating the base with an appropriate acid.

The starting materials employed in the aforedescribed method of preparation are either known compounds or can be prepared from known compounds by conventional methods. The hydroxy acids corresponding to the lactones of Formula I are described in U.S. patent application Ser. No. 363,455, P. Wei and S. Bell, filed on May 24, 1973 now U.S. Pat. No. 3,853,872.

When the compounds of the invention are employed pharmacologically, they may be administered alone or in combination with pharmaceutically acceptable carriers, the proportion of which is determined by the solubility and chemical nature of the compound, chosen route of administration, and standard pharmaceutical practice. For example, they may be administered orally in the form of tablets or capsules containing such exipients as starch, lactose, magnesium stearate, and so forth. They may be administered orally in the form of solution or they may be injected parenterally, e.g. intramuscularly. For parenteral administration, they may be used in the form of a sterile solution or suspensions containing other solutes, for example, enough saline or glucose to make the solution isotonic.

The dosage of the present pharmacologically active agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a dosage level that will generally afford effective results without causing any harmful or deleterious side effects.

The manner and process for making and using the invention are illustrated in the following examples, where all temperatures are given in degrees Centigrade.

EXAMPLE I 3-(p-Chlorophenyl)-2,3,5,6,7,8-Hexahydro-3-Hydroxy-thiazolo [3,2-a][1,3]Diazepin-2-Acetic Acid γ-Lactone, Hydrobromide 3-Bromo-3-p-chlorobenzoylpropionic acid (5.8 g, 0.02 m) and 3,4,5,6-tetrahydro-2-mercapto-1,3-diazepine (2.6 g, 0.02 m) are dissolved in 50 ml of acetic anhydride. The solution is heated on a steam bath for one-half hour and then cooled. Anhydrous ether (150 ml) is added to precipitate a heavy oil residue. After the solvent is decanted, the oily residue is treated with cold acetonitrile and collected. The crude material (3.7 g) is recrystallized by dissolving it in acetonitrile at room temperature and then concentrating the solution to a small volume. The solid is collected and washed with a small amount of acetonitrile to give the title compound, m.p. 183°–185°.

Analysis for: $C_{15}H_{15}N_2O_2ClS \cdot HBr$.
Calculated: C, 44.62; H, 4.00; N, 6.94 %.
Found: C, 44.88; H, 3.91; N, 6.81.
IR (KBr): lactone 5.5 μ; NMR (CDCl$_3$): δ7.7 (m, 4, aromatic); 5.0 (t, l, methine); 3.7 (m, 6, NCH$_2$CCH$_2$N); 2.1 (*m*, 3, CCH$_2$C); also exchangeable upfield.

EXAMPLE II 3-(p-chlorophenyl-2,3,6,7,-Tetrahydro-3-Hydroxy-5H-Thiazolo[3,2-a]Pyrimidine-2-Acetic Acid γ-Lactone, Hydrobromide 3-Bromo-3-(p-chlorobenzoyl)propionic acid (11.64 g, 0.04 m) and 2-mercapto-3,4,5,6-tetrahydropyrimidine (4.64 g, 0.04 m) are dissolved in 100 ml of glacial acetic acid containing 25 ml of acetic anhydride. The solution is heated on a steam bath for 15 minutes and then treated with Darco. The mixture is filtered, and the filtrate evaporated to give a residual solid which is treated with ether, dimethoxyethane, and acetonitrile. Recrystallization from acetonitrile gives the title compound, m.p. 200°–202°.

Analysis for: C$_{14}$H$_{13}$ClN$_2$O$_2$S.HBr

Calculated: C, 43.15; H, 3.62; N, 7.19; Cl, 9.10; S, 8.23 %.

Found: C, 42.81; H, 3.65; N, 7.26; Cl, 8.78; S, 8.22.

IR (KBr): Amine HBr, 3.5 μ; γ-lactone, 5.55 μ; C=N, 6.1 μ

EXAMPLE III

The CNS-effects of the compounds of Formula I are elicited and demonstrated by the following test procedure:

A compound of Formula I is administered orally (P.O.) or intraperitoneally (I.P.) to each of three mice. The animals are observed for signs of CNS-depressant activity, such as decreased motor activity, sedation, ataxia, loss of righting reflex, and decreased respiration. When tested as above-described, 3-(p-chlorophenyl-2,3,5,6,7,8-hexahydro-3-hydroxy-thiazolo[3,2-a]-8 1,3]diazepin-2-acetic acid γ-lactone, hydrobromide showed decreased motor activity and decreased respiration at 40 mg/kg (I.P.); and 3-(p-chlorophenyl-2,3,6,7-tetrahydro-3-hydroxy-5H-thiazolo[3,2-a]pyrimidine-2-acetic acid γ-lactone, hydrobromide showed decreased motor activity and decreased respiration at 40 mg/kg (P.O.) and ataxia and loss of righting reflex at 127 mg/kg (P.O.).

The ability of 3-(p-chlorophenyl-2,3,5,6,7,8-hexahydro-3-hydroxy-thiazolo[3,2-a][1,3]diazepin-2-acetic acid γ-lactone, hydrobromide and 3-(p-chlorophenyl-2,3,6,7-tetrahydro-3-hydroxy-5H-thiazolo[3,2-a]pyrimidine-2-acetic acid γ-lactone, hydrobromide to antagonize reserpine-induced ptosis is demonstrated as follows:

The compound is administered orally at graded dose levels to groups of six mice (3 males and 3 females) at a number of dose levels. One hour later the animals are challenged with reserpine, 2.5 mg/kg, I.P. The degree of ptosis for each eye is determined at 1 hour and 2 hours post-treatment. Prevention of ptosis is determined for each time period by comparison with controls run simultaneously. The percent antagonism is calculated as $$100 \times \frac{\text{Average score (control)} - \text{average score (test)}}{\text{average score (control)}}$$

When tested as above, 3-(p-chlorophenyl)-2,3,5,6,7,8-hexahydro-3-hydroxy-thiazolo[3,2-a][1,3]diazepin-2acetic acid γ-lactone, hydrobromide produces 50% antagonism at a dose of 27 mg/kg, while 3-(p-chlorophenyl-2,3,6,7-tetrahydro-3-hydroxy-5H-thiazolo[3,2-a]pyrimidine-2-acetic acid γ-lactone, hydrobromide produces 50% antagonism at a dose of 0.54 mg/kg.

What is claimed is:

1. A compound of the formula:

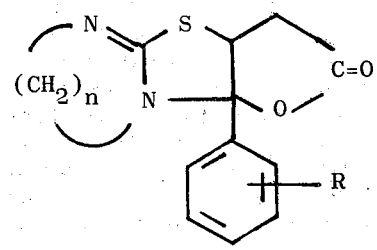

wherein R is hydrogen, chloro, bromo, iodo, nitro, trifluoromethyl, or alkoxy, said alkyl or alkoxy groups having from 1 to 4 carbons; and *n* is 2, 3, or 4; and the non-toxic pharmaceutically acceptable acid addition salts thereof.

2. The compound as defined in claim 1, which is: 3-(p-chlorophenyl)-2,3,5,6,7,8-hexahydro-3-hydroxy-thiazolo[3,2-a]-[1,3]diazepin-2-acetic acid γ-lactone.

3. The compound as defined in claim 1, which is: 3-(p-chlorophenyl-2,3,6,7-tetrahydro-3-hydroxy-5H-thiazolo[3,2-a]-pyrimidine-2-acetic acid γ-lactone.

* * * * *